United States Patent
Steffen

(10) Patent No.: US 8,425,411 B2
(45) Date of Patent: Apr. 23, 2013

(54) WINDOWED FLEXOR TENDON SHEATH RETRACTOR AND DILATOR

(76) Inventor: Dennis L. Steffen, Tavernier, FL (US)

( * ) Notice: Subject to any disclaimer, the term of this patent is extended or adjusted under 35 U.S.C. 154(b) by 259 days.

(21) Appl. No.: 12/942,348

(22) Filed: Nov. 9, 2010

(65) Prior Publication Data

US 2011/0112532 A1 May 12, 2011

Related U.S. Application Data

(60) Provisional application No. 61/259,665, filed on Nov. 10, 2009.

(51) Int. Cl.
*A61B 1/32* (2006.01)

(52) U.S. Cl.
USPC .......................... 600/203; 600/210; 606/86 R

(58) Field of Classification Search .................. 606/206, 606/215, 216; 600/206, 215, 216, 203, 210, 600/235
See application file for complete search history.

(56) References Cited

U.S. PATENT DOCUMENTS

| | | | |
|---|---|---|---|
| 8,075,575 B2 * | 12/2011 | Gonzalez-Hernandez | ... 606/148 |
| 8,251,901 B2 * | 8/2012 | White et al. | ................. 600/210 |
| 2009/0048616 A1 * | 2/2009 | Gonzalez-Hernandez | ... 606/148 |
| 2010/0137883 A1 * | 6/2010 | Gonzalez-Hernandez | ... 606/138 |
| 2011/0015656 A1 * | 1/2011 | Gonzalez-Hernandez | ... 606/148 |

* cited by examiner

*Primary Examiner* — Andrew Yang

(57) ABSTRACT

A surgical device and method used to assist in the surgical repair of damaged and/or severed tendons. In the present invention, the device is comprised of a distal conical member, having an inner and outer surface, a tapered tip, a rounded end, and windowed openings on either side of axial centerline passing through the inner and outer surfaces. In the same embodiment, the device is comprised of a proximal concave convex member with an inner and outer surface, a tapered tip, and a rounded end, tapering both in width and thickness to the tip. The present invention further discloses a method of passing a severed flexor tendon through the tendon sheathing to the repair site aiding in the passage of the severed tendon through the edges of the pulleys in the flexor tendon sheath, wherein the distal conical member of the device disclosed in the present invention is introduced into the edge of a flexor tendon sheath's pulley and a severed tendon end is passed along the inner surface of the conical member allowing the tendon to be reintroduced into the sheathing with minimal trauma. The present invention further discloses a method of dilation of the pulleys in the flexor tendon sheath, wherein the proximal concave convex member of the device disclosed in the present invention is introduced into the edge of a flexor tendon sheath's pulley to a desire depth and left in place until the desired amount of dilation is achieved the tendon is then introduced back into the sheathing utilizing the afore described method.

4 Claims, 5 Drawing Sheets

WINDOWED FLEXOR TENDON SHEATH RETRACTOR AND DILATOR

CROSS REFERENCES TO RELATED APPLICATIONS

This application claims the benefit under 35 U.S.C. §119 (e) of U.S. Provisional Application No. 61/259,665, filed on Nov. 10, 2009, the complete disclosure of which is incorporated herein by reference in its entirety.

FIELD OF THE INVENTION

The present invention relates to a surgical device and method used to assist in the surgical repair of damaged and/or severed tendons.

INTRODUCTION

In the hand, the fingers are moved by flexor and extensor tendons arising from muscles in the forearm. The flexor tendon mechanism reveals three main components: 1) the skeleton, including the bones and the articulations or joints between the bones; 2) a tunnel or pulley system for the tendon; and 3) the tendon itself.

There are two flexor tendons in each finger which work to flex the proximal and distal interphalangeal joints, namely the flexor digitorum superficialis and the flexor digitorum profundus respectively.

A fibrous sheath holds the flexors tendons in close proximity to the phalanges of each finger to ensure that their pull produces immediate movement at the interphalangeal joint.

The flexor tendon sheath tissue is anchored to the bone and forms a smooth but tight fibrous tunnel which the flexor tendon moves within. The flexor tendon sheath is not a uniform fibrous tunnel, but rather, is made of identifiable segments. The individual segments that make up the flexor tendon sheath are referred to as pulleys because of the mechanical role they play: holding the tendons close to the bone; preventing "bow-stringing" of the tendons; and ultimately translating the flexor tendon pull into joint motion.

For decades, the lack of specialized instruments for surgical repair of severed tendons in the region of the hand containing the flexor tendon and the flexor tendon sheath has proven challenging and, to date, the results of such repairs are usually less optimal. One of the main reasons for the characteristics associated with a less optimal repair involves the technique associated with the retrieval of the free end of the severed tendon. In order for the repair to be made the free end must first be located (as it typically retracts in the direction of the palm of the hand when severed). Once located the free end of tendon needs to be jointed with the opposite severed portion (repair site). To do this the surgeon must feed the free end back through the sheathing and pulling system. The surgeon will usually attach a suture to the free end and pull it back to the repair site feeding it through the pulley system as they work their way back to the repair site. With current methods and instruments the tip of the free end usually ends up with a frayed appearance after being feed through the restrictive areas and sharp edges of the pulley system. This frayed end then interns makes for an undesirable bulky repair. One attempt at improving this procedure described in Patent Application No. 20090048616 discloses a retractor for use in the placement of an implant.

BRIEF DESCRIPTION

The invention provides a device and method for flexor tendon repair. The majority of publications addressing flexor tendon repair focus on the strength of repairs regarding various suture techniques. It is well known that the prognosis for a tendon repair is more predictable and generally better when the laceration to the tendon has taken place in a portion of the tendon that is not located within the flexor tendon sheath; for example, in the palm or the forearm. The portion of the tendon within the flexor tendon sheath can be difficult with unpredictable outcomes. It is the goal of the present invention to provide a device and method that will facilitate the manipulation of a severed tendon free end during surgery and greatly improve the overall outcome of the procedure.

In one embodiment of the present invention is a device comprised of a conical shaped feature (Retractor), having an inner and outer surface, a flared proximal end and a tapered distal tip, a handle is joined to the proximal end with a Dilator similar in proportion and shape of the Retractor is located at the opposite end. In a preferred embodiment of the present invention, the Retractor is further comprised of two openings. These two openings act as windows for improved visibility of the tendon during the procedure. The two windows also reduce the surface area of the inner surface thus reducing drag on the tendon as it is pulled back into the sheathing and pulley system. During a flexor tendon repair procedure involving a severed tendon, the distal tip of the Retractor is introduced into the pulley and placed directly adjacent to the free end of the tendon. The proximal flared end of the Retractor acts as a guide to aid in the introduction of the free end of the tendon back into the sheathing and pulley system. When an inflamed and/or engorged tendon end, that otherwise may not easily pass through the edge of a pulley, can be placed into the proximal flared end of the device and gently compressed wherein the tendon end will be simultaneously squeezed into the pulley in a gentler manner.

In another aspect, the invention provides a method of dilation of the sheath and pulley system through the use of the Dilator located on the opposite end of the handle. As stated previously the Dilator is shaped and proportioned similar to the Retractor. The Dilator would be placed in areas of concern (primarily pulleys) where the surgeon may feel restrictions related to the passing of the tendon during the procedure may occur. The surgeon would place the Dilator in the desired location for the desired length of time necessary to sufficiently reduce the restriction.

Other advantages and a better appreciation of the specific adaptations, variations, and physical attributes of the invention will be gained upon an examination of the following detailed description of the invention, taken in conjunction with the accompanying drawings.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

Figure 1:
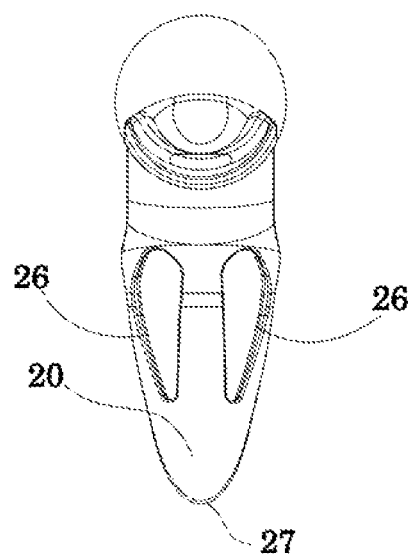
FIG. 1 is a top plan view of Windowed Retractor conical feature configuration with a plurality of openings, a tapered tip rounded at the most distal end, all in accordance with the invention.

A flexor tendon sheath retractor & dilator embodying the principles of the invention is provided.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

As used herein, the term "conical feature" is meant to refer to tapered shape geometry having a large diameter at one end and a small diameter at the opposite.

In view of the foregoing disadvantages inherent in conventional retractors and dilators, the invention provides a novel system and method for repair of flexor tendons. The invention provides a instrument specifically designed and proportioned for use in this area.

Reference is now made to FIGS. 1-5 in which a flexor tendon sheath retractor and dilator, generally designated by reference numeral 10, in accordance with the invention is shown. System 10 includes a retractor 20, a dilator 21 and a handle 28 for manipulation of the instrument. In an illustrated embodiment, retractor 20 is defined by a first surface 22 and a second, tendon-contacting surface 24 that is opposed to the first surface 22. In an illustrated embodiment, dilator 21 is defined by a first surface 32 and a second, sheath-contacting surface 30 that is opposed to the first surface 32.

Retractor 20 includes a plurality of apertures or windows 26 which extend through the first and second surfaces 22, 24 of retractor 20. Each of the apertures 26 has a predefined shape and size. For instance, each of the apertures 26 suitably shaped as, e.g., following the contour of the retractor profile as illustrated. As shown in FIG. 1, these apertures 26 reduce the overall surface area more precisely the surface area of surface 24. The reduction of this surface area reduces the drag coefficient seen as the tendon is pulled pass it. The apertures further increase the visibility of the tendon as it is feed through the sheathing and pulley system. Also shown in FIG. 1 the far distal tip 27 of the retractor 20 is tapered and curved to facilitate easier insertion into the sheath and pulley system.

Figure 2:
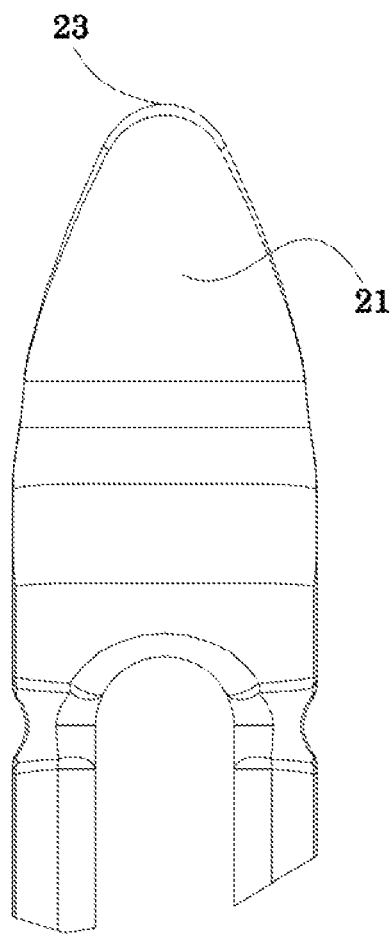
FIG. 2 is a top plan view of dilator configuration with tapered tip rounded at the most distal end, all in accordance with the invention.
Figure 3:
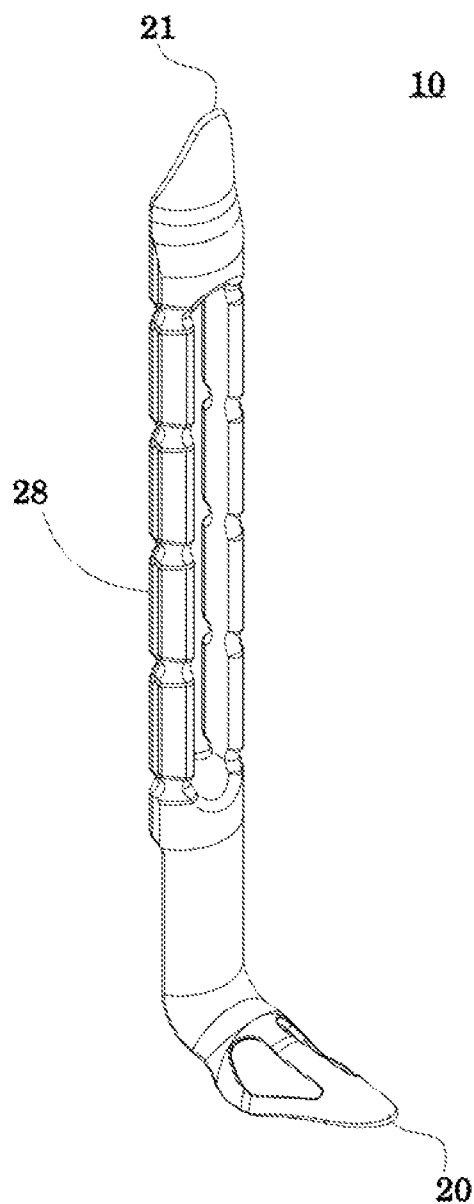
FIG. 3 depicts perspective view orientated with the retractor tip on the lower portion of the handle and the dilator tip on the upper portion of the handle configuration, all in accordance with the invention.

The dilator as shown in FIG. 2 shows the far distal tip 23 of the dilator 21 is tapered and curved to facilitate easier insertion into the sheath and pulley system.

Figure 4:
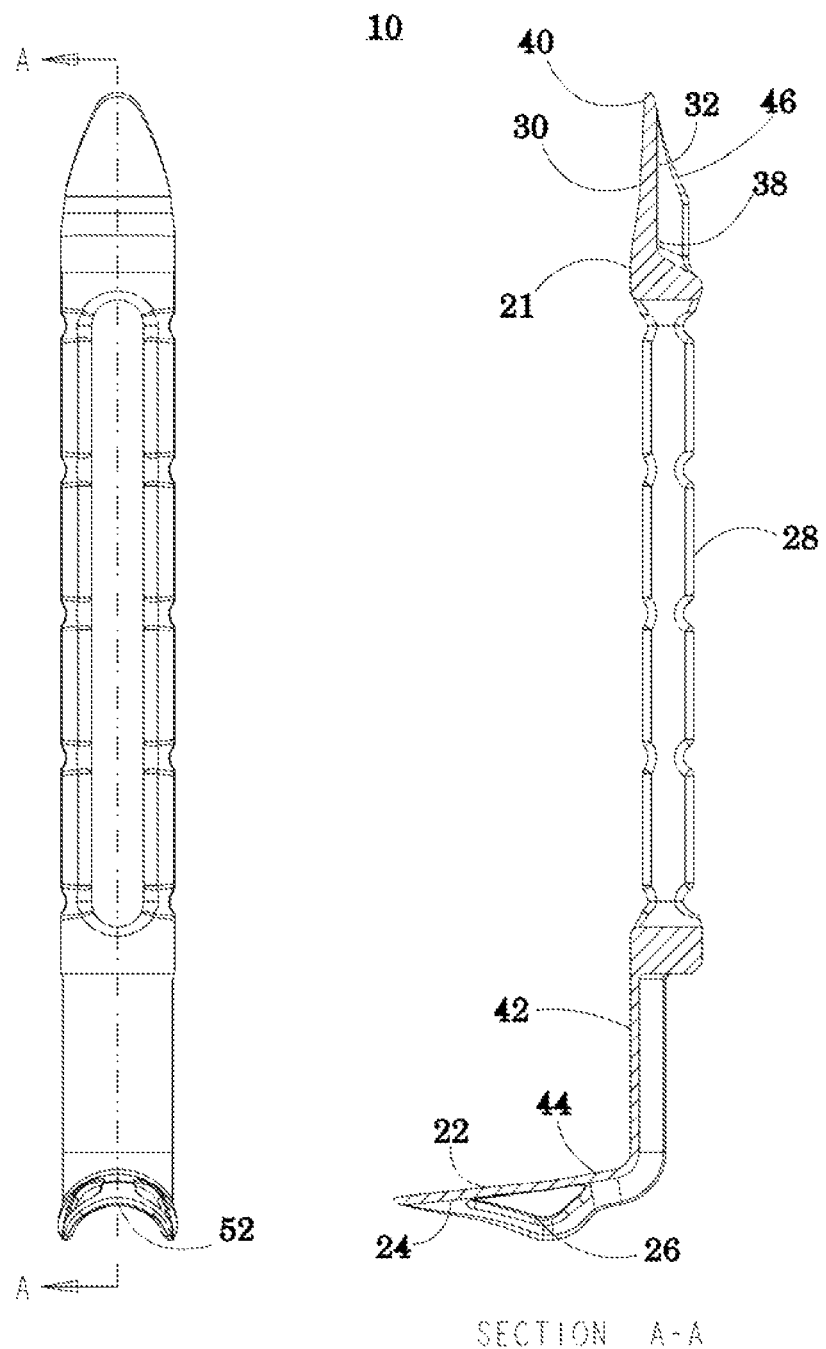
FIG. 4 is a front view with a side, cross-sectional view of the retractor and the dilator, illustrating the angle of the conical retractor and the taper of the dilator, all in accordance with the invention.

The dilator 21 is also tapered in thickness as shown in FIG. 4 thicker at proximal end 38 and thinner at distal tip 40. The profile of the dilator 21 also tapers 46 toward the distal tip.

Also shown in FIG. 4 the shank 42 which connects the retractor 20 to the handle 28 incorporates an angled approach 44 (lead-in) as it connects to the retractor 20.

Figure 5:
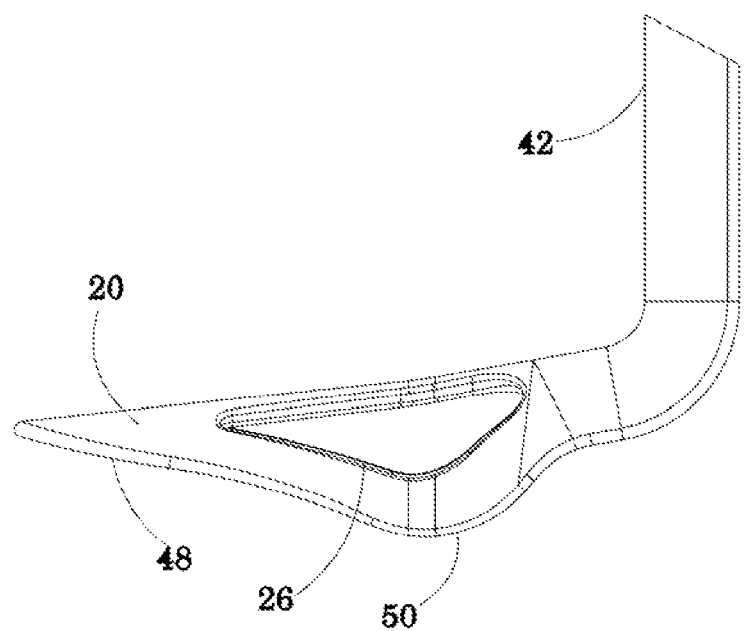
FIG. 5 illustrates a side view of the retractor profile depicting its contour, all in accordance with the invention.

As shown in FIG. 5 the profile of the retractor 20 also tapers 48 toward the distal tip. The profile of the retractor 20 also displays another important feature a skirt area 50 to facilitate in the spreading of the sheath and pulley system and to aid in the transition of the tendon back into the system.

Retractors 20 may have many shapes. As shown in FIG. 4, retractors 20 may have a suitably conical shape 52 with, e.g., an arched cross section contouring the bone surface.

In practice, the invention provides a method of retraction of the sheathing and pulley system associated to repair of flexor tendons.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The invention claimed is:

1. A surgical device comprising: a far distal conical member with contoured dual apertures further comprising an inner and outer surface and tapering to a rounded tip also included a far proximal member further comprising a concave inner and convex outer surface tapering in both width and thickness to a rounded tip.

2. The surgical device of claim 1, further comprising a handle with an opposed approach attached to said conical member.

3. The surgical device of claim 1, farther comprising a plurality of windowed openings on either side of the axial centerline of the said conical member.

4. The surgical device of claim 1, further comprising a handle attached to said concave convex member.

\* \* \* \* \*